(12) United States Patent
Leschine et al.

(10) Patent No.: US 7,682,811 B2
(45) Date of Patent: Mar. 23, 2010

(54) SYSTEMS AND METHODS FOR PRODUCING BIOFUELS AND RELATED MATERIALS

(75) Inventors: Susan Leschine, Leverett, MA (US); Thomas A. Warnick, Sunderland, MA (US)

(73) Assignee: University of Massachusetts, Boston, MA (US)

( * ) Notice: Subject to any disclaimer, the term of this patent is extended or adjusted under 35 U.S.C. 154(b) by 62 days.

(21) Appl. No.: 11/698,727

(22) Filed: Jan. 26, 2007

(65) Prior Publication Data

US 2007/0178569 A1 Aug. 2, 2007

Related U.S. Application Data

(60) Provisional application No. 60/762,813, filed on Jan. 27, 2006.

(51) Int. Cl.
*C12P 7/06* (2006.01)
*C12P 7/08* (2006.01)
*C12P 7/10* (2006.01)

(52) U.S. Cl. .................. 435/161; 435/163; 435/165

(58) Field of Classification Search ................ None
See application file for complete search history.

(56) References Cited

U.S. PATENT DOCUMENTS

| 5,138,007 A | 8/1992 | Meister |
| 5,837,506 A | 11/1998 | Lynd et al. |
| 6,660,506 B2 | 12/2003 | Nguyen et al. |

FOREIGN PATENT DOCUMENTS

WO  WO 2007/130984 A2  11/2007

OTHER PUBLICATIONS

Leschine, "The diversity of soil microbes holds the key to advancing bioenergy production". Geological Society of America Joint Meeting, Houston, Oct. 8, 2008.
Leschine, "A novel biocatalyst for Cellulosic Ethanol Production", First Annual TIMBR Conference on Cellulosic Biofuels, University of Massachusetts Amherst, Sep. 19, 2008.
Leschine, "Clostridium phytofermentans: A novel catalyst for cellulosic ethanol production" Georgia State University Biotechnology Symposium, Atlanta Aug. 14, 2008.
Leschine, "A novel microbial catalyst for advanced biofuel production", Advanced Biofuels Workshop and Trade Show, Minneapolis, Aug. 12, 2008.
Leschine, "A Novel Microbial Catalyst for Cellulosic Ethanol Production", Agriculture and Energy Seminar Series, USDA, Washington, D.C., Jan. 23, 2008.
Leschine, "A novel consolidated bioprocessing technology for biomass ethanol production", Biotechnology Industry Organization (Bio), Pacific Rim Conference, Honolulu, Nov. 15, 2007.
Leschine, "Testimony of Susan Leschine", Testimony Before the Select Committee on Energy Independence and Global Warming, Hearing on The Gas is Greener: the Future of Biofuels, Oct. 24, 2007.
Leschine, "Biomass to Biofuel Technology: A Novel Bacterial Catalyst for Consolidated Bioprocessing of Biomass to Ethanol", The Institute for Massachusetts Biofuels Research (TIMBR) University of Massachusetts Amherst, Jan. 2007.
Shaw et al., "Metabolic Engineering of the Xylose Utilizing Thermophile Thermoanaerobacerium Saccharolyticum Jw/S1-Ys485 for Ethanol Production", Advances in Metabolic Engineering and Bioinformatics: From Prokaryotes to Eukaryotes The Preliminary Program for 2005 Annual Meeting (Cincinnati, OH) (abstract only).
Lynd et al. in "Consolidated Bioprocessing of Cellulosic Biomass: An Update," Current Opinion in Biotechnology, 16:577-583, 2005.
Mosier et al., "Features of promising technologies for pretreatment of lignocellulose biomass", Bioresource Technology, 96, 673-686, 2005.
T. Juhasz, "Production of β-Glucosidase in Mixed Culture of *Aspergillus niger* BKMF 1305 and *Trichoderma reesei* RUT C30", Food Tech. Biotechnol. 41 (1), pp. 41-53, 2003.
Martin et al., "Ethanol production from enzymatic hydrolysates of sugarcane bagasse using recombinant xylose-utilising *Saccharomyes cerevisiae*", Enzyme and Microbial Technology, 31:274-282, 2002.
Kim et al., "Effects of Pressing Lignocellulosic Biomass on Sugar Yield in Two-Stage Dilute-Acid Hydrolysis Process", Biotechnol. Prog., 18, pp. 489-494, 2002.
Desvaux et al., "Cellulose Catabolism by *Clostridium cellulolyticum* Growing in Batch Culture on Defined Medium", Applied and Environmental Microbiology, vol. 66, No. 6, pp. 2461-2470, 2000.
Sheehan et al., "Enzymes, Energy, and the Environment: A Strategic Perspective on the U.S. Department of Energy's Research and Development Activities for Bioethanol", Biotechnology Progress, 15pp. 817-827, 1999.

(Continued)

*Primary Examiner*—Vera Afremova
(74) *Attorney, Agent, or Firm*—Fish & Richardson P.C.

(57) ABSTRACT

*Clostridium phytofermentans* cells (American Type Culture Collection 700394$^T$) and all other strains of the species can ferment materials such as biomass into useful products and coproducts, such as ethanol, hydrogen and organic acids. Compositions that include *Clostridium phytofermentans* are also disclosed.

13 Claims, 7 Drawing Sheets

OTHER PUBLICATIONS

Bjerre, "Pretreatment of Wheat Straw using Combined Wet Oxidation and Alkaline Hydrolysis Resulting in Convertible Cellulose and Hemicellulose", Biotechnology and Bioengineering, vol. 49, pp. 568-577, 1996.

Leschine et al., "Ethanol Production from Celluolose by a Coculture of *Zymomonas mobilis* and a Clostridum", Current Microbiology, vol. 11, pp. 129-136, 1984.

Wolin et al., "Viologen Dye Inhibition of Methane Formation by Methanobacillus Omelianskil", Journal of Bacteriology, 87:993, pp. 993-998, 1964.

Greer, "Creating Cellulosic Ethanol—Spinning Straw Into Fuel," BioCycle, 61-65 (2005).

Knauf and Moniruzzaman, "Lignocellulosic biomass processing: A perspective," Int. Sugar Journal 106(1263):147-150 (2004).

Lynd et al., "Microbial cellulose utilization: fundamentals and biotechnology," Microbiol. Mol. Biol. Rev. 66(3):506-77 (2002), table of contents. Review. Erratum in: Microbiol. Mol. Biol. Rev. Dec. 2002;66(4):739.

Ralph, "Lignin Structure: Recent Developments," (US Dairy Forage Research Center, USDA-Agricultural Research Service), (1999).

Stackebrandt and Goebel, "Taxonomic Note: A Place for DNA-DNA Reassociation and 16S rRNA Sequence Analysis in the Present Species Definition in Bacteriology," Int. J. Sys. Bact. 44(4):846-849 (1994).

Warnick et al., "*Clostridium phytofermentans* sp. nov., a cellulolytic mesophile from forest soil," Int. J. Syst. Evol. Microbiol. 52(Pt 4):1155-1160 (2002).

Mai et al., "Advances in Development of a Genetic System for Thermoanaerobacerium spp.: Expression of Genes Encoding Hydrolytic Enzymes, Development of a Second Shuttle Vector, and Integration of Genes into the Chromosome", Applied and Environmental Microbiology, vol. 66(11): pp. 4817-4821, Nov. 2000.

SYSTEMS AND METHODS FOR PRODUCING BIOFUELS AND RELATED MATERIALS

CROSS REFERENCE TO RELATED APPLICATION

This application claims the benefit of priority from U.S. Provisional Patent Application No. 60/762,813, filed on Jan. 27, 2006, the contents of which is incorporated herein by reference in its entirety.

STATEMENT AS TO FEDERALLY SPONSORED RESEARCH

This invention was made with Government support under Grant No. DE-FG02-02ER15330, awarded by the United States Department of Energy (DOE). The Government thus has certain rights in the invention.

TECHNICAL FIELD

This invention relates to compositions, and to systems and methods for producing biofuels such as ethanol, and related materials.

BACKGROUND

There is an interest in developing methods of producing usable energy from renewable and sustainable biomass resources. Energy in the form of carbohydrates can be found in waste biomass, and in dedicated energy crops, such as grains (e.g., corn or wheat) or grasses (e.g., switchgrass). Cellulosic and lignocellulosic materials, are produced, processed, and used in large quantities in a number of applications.

A current challenge is to develop viable and economical strategies for the conversion of carbohydrates into usable energy forms. Strategies for deriving useful energy from carbohydrates include the production of ethanol ("cellulosic ethanol") and other alcohols (e.g., butanol), conversion of carbohydrates into hydrogen, and direct conversion of carbohydrates into electrical energy through fuel cells. For example, biomass ethanol strategies are described by DiPardo, *Journal of Outlook for Biomass Ethanol Production and Demand (EIA Forecasts)*, 2002; Sheehan, *Biotechnology Progress*, 15:8179, 1999; Martin, *Enzyme Microbes Technology*, 31:274, 2002; Greer, *BioCycle*, 61-65, April 2005; Lynd, *Microbiology and Molecular Biology Reviews*, 66:3, 506-577, 2002; and Lynd et al. in "Consolidated Bioprocessing of Cellulosic Biomass: An Update," *Current Opinion in Biotechnology*, 16:577-583, 2005.

SUMMARY

The invention is based, in part, on the discovery of new characteristics of an anaerobic bacterium, *Clostridium phytofermentans*. For example, an isolated strain of *Clostridium phytofermentans* (ISDg$^T$, American Type Culture Collection 700394$^T$) has been deposited under conditions that assure that access to the cultures will be available during the pendency of the patent application to one determined by the Commissioner of Patents and Trademarks to be entitled thereto under 37 C.F.R. 1.14 and 35 U.S.C. 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action. Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposits, and in any case, for a period of at least 30 (thirty) years after the date of deposit or for the enforceable life of any patent which may issue disclosing the cultures plus five years after the last request for a sample from the deposit. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

We have found that *Clostridium phytofermentans*, such as strain ISDg$^T$, alone or in combination with one or more other microbes (e.g., yeasts or other bacteria) can ferment a material that is or includes a carbohydrate, or a mixture of carbohydrates, into a combustible fuel, e.g., ethanol, propanol and/or hydrogen, on a large scale. For example, *Clostridium phytofermentans* can ferment waste biomass, such as saw dust, wood flour, wood pulp, paper pulp, paper pulp waste steams, grasses (e.g., switchgrass), biomass plants and crops (e.g., Crambe), algae, rice hulls, bagasse, jute, leaves, grass clippings, corn stover, corn cobs, corn grain (corn grind), distillers grains, and distillers solutes, into ethanol, propanol and hydrogen. In addition, other useful organic products can also be produced, such as organic acids (e.g., formic acid, lactic acid and acetic acid), or their conjugate bases (e.g., formate, lactate or acetate).

In one aspect, the invention features methods of making a fuel or fuels from one or more biomass materials providing a biomass material that includes a high molecular weight carbohydrate; hydrolyzing the biomass material to provide a hydrolyzed biomass material; combining the hydrolyzed biomass material with *Clostridium phytofermentans* cells in a medium; and fermenting the hydrolyzed biomass material under conditions and for a time sufficient to produce a fuel or a mixture of fuels, e.g., ethanol, propanol, and/or hydrogen. In addition to fuels, other products and/or coproducts can be produced (e.g., organic acids and/or their conjugate bases). In some embodiments, a concentration of carbohydrates in the medium is greater than about 20 mM. In other embodiments, the concentration is greater than about 1 mM, e.g., greater than 2, 3, 4, 5, 6, 7, 8, 9, 10, 12, 14, 16, or greater than about 18 mM.

In another aspect, the invention features a fuel plant that includes a hydrolysis unit configured to hydrolyze a biomass material that includes a high molecular weight carbohydrate, and a fermentor configured to house a medium and contains *Clostridium phytofermentans* cells dispersed therein.

In another aspect, the invention features methods of making a fuel or fuels that include combining *Clostridium phytofermentans* cells and a lignocellulosic material (and/or other biomass material) in a medium, and fermenting the lignocellulosic material under conditions and for a time sufficient to produce a fuel or fuels, e.g., ethanol, propanol and/or hydrogen.

In another aspect, the invention features methods of making a fuel or fuels that include combining *Clostridium phytofermentans* cells and a material that includes a carbohydrate in a medium, and fermenting the material including the carbohydrate under conditions and for a time sufficient to produce a fuel. A concentration of the carbohydrate in the medium is greater than 20 mM, e.g., greater than 30 mM, 40 mM, 50 mM, 75 mM, or even 100 mM or more.

In any of the methods described herein, *Clostridium phytofermentans* cells can be utilized alone or in combination with one or more other microbes (e.g., yeasts or other bacteria) to produce a fuel or another useful product, such as organic acids or their conjugate bases, which can be isolated as salts (e.g., sodium or potassium salts). An example of another bacterium is any strain of *Zymomonas mobilis*.

In another aspect, the invention features methods of making a fuel or fuels from one or more biomass materials with *Clostridium phytofermentans* alone or in coculture with one or more other microbes, such as a yeast strain or a strain of *Zymomonas mobilis*. In addition to making fuels, the coculture can be used to make any coproduct described herein, such as an organic acid, or a conjugate base or salt thereof.

In another aspect, the invention features methods of employing *Clostridium phytofermentans* to produce an organic acid, or a conjugate base or salt thereof, from one or more biomass materials, such as any of those materials described herein. For example, the other useful products or coproducts can be used as feedstocks for the chemical or pharmaceutical industries. Examples of acids (conjugate bases) that can be produced include lactic acid (lactate) and acetic acid (acetate).

In another aspect, the invention features cocultures that include *Clostridium phytofermentans* and one or more other microbes, e.g., yeasts or other bacteria (e.g., *Zymomonas mobilis*).

In another aspect, the invention features compositions that include *Clostridium phytofermentans* and one or more other microbes, e.g., yeasts or other bacteria (e.g., *Zymomonas mobilis*). The composition can be, e.g., in the form of a solid mixture (e.g., a freeze-dried mixture), or a liquid dispersion of the microbes, e.g., a coculture.

In another aspect, the invention features methods of making a useful product, such as a biofuel, that include selecting a biomass or a mixture of biomass materials; combining the biomass with a medium that includes *Clostridium phytofermentans*; fermenting the biomass for a first period of time to provide a second biomass material; combining the second biomass material (with or without the *Clostridium phytofermentans*) with another microbe or a mixture of microbes different from *Clostridium phytofermentans*; and then fermenting the second biomass for a second period of time to produce a useful material, such as a fuel or an organic acid.

In another aspect, the invention features fermentors that include a medium that includes *Clostridium phytofermentans* dispersed therein. Along with *Clostridium phytofermentans*, the medium can include one or more of any of the other microbes described herein.

In another aspect, the invention features fermentors that include *Clostridium phytofermentans* in coculture with one or more of any of the other microbes described herein.

In another aspect, the invention features fermentors that include a medium that includes *Clostridium phytofermentans* dispersed therein. The fermentors are configured to continuously remove a fermentation product, such as ethanol. In some embodiments, the concentration of the product remains substantially constant, or within about twenty five percent of an average concentration. In some embodiments, any biomass described herein is continuously fed to the fermentor.

In another aspect, the invention features products made by any of the processes described herein.

In another aspect, the invention features kits, e.g., for seeding a fermentor, that include *Clostridium phytofermentans*. The kits can further include any one or more of any of the other microbes described herein. For example, the microbes in the kits can be combined in a single container or multiple containers. The microbes in the kits can be dispersed in a medium, or they can be freeze-dried. The kits can further include starter materials, such as nutrients.

*Clostridium phytofermentans* (American Type Culture Collection 700394$^T$) is defined based on the phenotypic and genotypic characteristics of a cultured strain, ISDg$^T$ (Warnick et al., *International Journal of Systematic and Evolutionary Microbiology*, 52:1155-60, 2002). The invention generally relates to systems, and methods and compositions for producing fuels and/or other useful organic products involving strain ISDg$^T$ and/or any other strain of the species *Clostridium phytofermentans*, which may be derived from strain ISDg$^T$ or separately isolated. The species is defined using standard taxonomic considerations (Stackebrandt and Goebel, *International Journal of Systematic Bacteriology*, 44:846-9, 1994): Strains with 16S rRNA sequence homology values of 97% and higher as compared to the type strain (ISDg$^T$) are considered strains of *Clostridium phytofermentans*, unless they are shown to have DNA re-association values of less than 70%. Considerable evidence exists to indicate that microbes which have 70% or greater DNA re-association values also have at least 96% DNA sequence identity and share phenotypic traits defining a species. Analyses of the genome sequence of *Clostridium phytofermentans* strain ISDg$^T$ indicate the presence of large numbers of genes and genetic loci that are likely to be involved in mechanisms and pathways for plant polysaccharide fermentation, giving rise to the unusual fermentation properties of this microbe. Based on the above-mentioned taxonomic considerations, all strains of the species *Clostridium phytofermentans* would also possess all, or nearly all, of these fermentation properties. *Clostridium phytofermentans* strains can be natural isolates, or genetically modified strains.

Advantages of the new systems and methods include any one of, or combinations of, the following. *Clostridium phytofermentans* can ferment a broad spectrum of materials into fuels with high efficiency. Advantageously, waste products, e.g., lactose, waste paper, leaves, grass clippings, and/or sawdust, can be used to make fuels. *Clostridium phytofermentans* remains active even at high concentrations of carbohydrates. Often materials that include carbohydrates can be used raw, without pretreatment. For example, in some instances, it is not necessary to pretreat the cellulosic material with an acid, a base, or an enzyme to release the lower molecular weight sugars that form part of the cellulosic material prior to fermentation. Instead, *Clostridium phytofermentans* can ferment the raw cellulosic material into a fuel directly. In some instances, lignocellulosic materials, e.g., sawdust or switchgrass, can be used without removal of lignin, and/or hemicelluloses. *Clostridium phytofermentans* cells grow and ferment under a wide range of temperatures and pH ranges. The pH of the fermentation medium may not need to be adjusted during fermentation. In some instances, *Clostridium phytofermentans* cells can be used in combination with one or more other microbes to increase the yield of a desired product, e.g., ethanol. In addition, *Clostridium phytofermentans* can ferment high concentrations of 5-carbon sugars, or polymers that include 5-carbon sugar repeat units, to combustible fuels. Five-carbon sugars, such as xylose, or polymers that include 5-carbon sugar repeat units, such as xylan and other components of the "hemicellulose" fraction of plant cell walls, are hydrolyzed and fermented by *Clostridium phytofermentans* concomitantly with other polymeric components of lignocellulosic materials yielding products such as ethanol and hydrogen. The 5-carbon sugars, or polymers that include 5-carbon sugar repeat units, do not appear to divert metabolic resources of *Clostridium phytofermentans*. Furthermore, *Clostridium phytofermentans* ferments higher cellulose concentrations, e.g., greater than 40 mM (glucose equivalents), with increasing ethanol yield. Other cellulose-fermenting microbes generally do not ferment higher concentrations of cellulose, above about 20 mM (glucose equivalents), and ethanol production decreases at higher cellulose concentrations (Desvaux et al., *Appl. Environ. Microbiology*, 66, 2461-2470, 2000).

Carbohydrates can be polymeric, oligomeric, dimeric, trimeric, or monomeric. When the carbohydrates are formed from more than a single repeat unit, each repeat unit can be the same or different. Examples of polymeric carbohydrates include cellulose, xylan, pectin, and starch, while cellobiose and lactose are examples of dimeric carbohydrates. Example of a monomeric carbohydrates include glucose and xylose. The term "low molecular weight carbohydrate" as used herein is any carbohydrate with a formula weight, or a number average molecular weight of less than about 1,000, as determined using a universal calibration curve. Generally, the term "high molecular weight carbohydrate" is any carbohydrate having a molecular weight of greater than 1,000, e.g., greater than 5,000, greater than 10,000, greater than 25,000, greater than 50,000, greater than 100,000, greater than 150,000, or greater than 250,000.

For carbohydrates having a defined single structure with a defined and computable formula weight, e.g., monomeric, or dimeric carbohydrates (e.g., arabinose and cellobiose, respectively), concentrations are calculated using the formula weight of the carbohydrate. For carbohydrates not having a defined single structure, e.g., polymeric carbohydrates (e.g., cellulose), concentrations are calculated assuming that the entire mass of the polymeric carbohydrate can be hydrolyzed to the monomeric carbohydrate unit from which the polymeric carbohydrate is formed. The formula weight of the monomeric carbohydrate unit is then applied to calculate the concentration in monomer equivalent units. For example, pure cellulose is made up entirely of glucose repeat units. 10 grams of cellulose would give 10 grams of glucose, assuming that the entire mass of the cellulose is hydrolyzed to glucose. Glucose ($C_6H_2O_6$) has a formula weight of 180.16 amu. 10 grams of glucose is 0.056 moles of glucose. If this amount of glucose is in 1 L of solution, the concentration would be 0.056 M or 56 mM. If the polymer has more than one repeat unit, the concentration would be calculated as a total average carbohydrate concentration by assuming that the entire mass of the polymeric carbohydrate can be hydrolyzed to the monomeric carbohydrate units from which the polymeric carbohydrate is formed. For example, if the polymeric carbohydrate is made up entirely of the two repeat units, hydrolysis of X grams of polymeric carbohydrate gives X grams of monomeric carbohydrates. A composite formula weight is the sum of the product of the mole fraction of the first monomeric carbohydrate and its formula weight and the product of the mole fraction of the second monomeric carbohydrate and its formula weight. The average number of moles of carbohydrates is then X grams divided by the composite formula weight. The average carbohydrate concentration is found by dividing the average number of moles by the quantity of solution in which they reside.

A "fermentable material" is one that *Clostridium phytofermentans* (e.g., $ISDg^T$) can, at least in part, convert into a fuel, e.g., ethanol, propanol or hydrogen and/or another useful product, e.g., an organic acid.

Biomass is an organic, non-fossilized material that is, or is derived from, biological organisms (e.g., plants or animals), dead or alive. Biomass excludes mass that has been transformed by geological processes into substances such as coal or petroleum, but includes materials that are derived from living or dead organisms, e.g., by chemically treating such organisms or remnants of such organisms. Examples of biomass include wood, wood-related materials (e.g., particle board), paper, grasses (e.g., switchgrass, *Miscanthus*), rice hulls, bagasse, cotton, jute, hemp, flax, bamboo, sisal, abaca, straw, leaves, grass clippings, corn stover, corn cobs, distillers grains, legume plants, sorghum, and biomass crops (e.g., Crambe).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
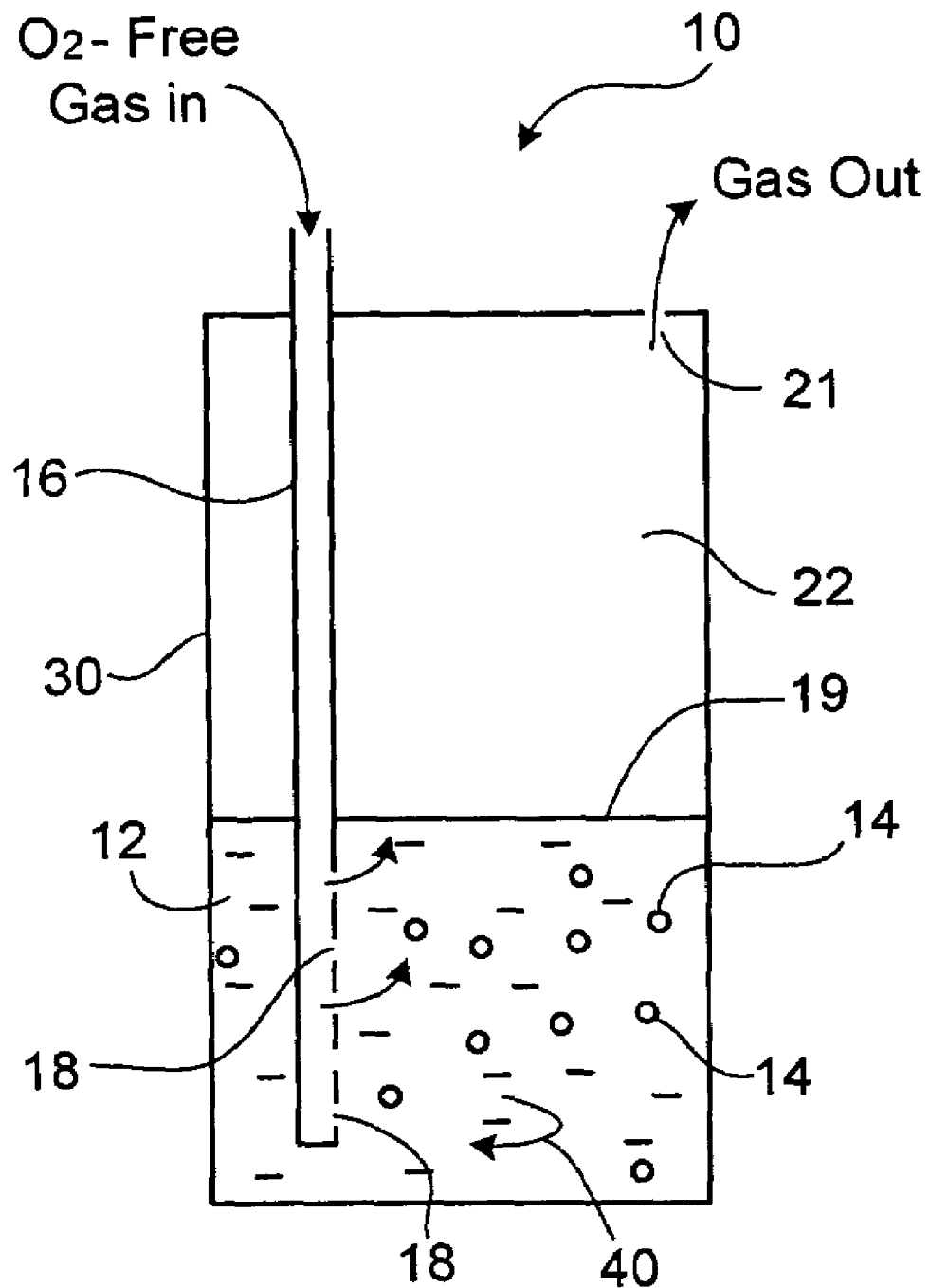
FIG. 1 is a schematic cross-sectional view of a fermentation vessel holding a medium having *Clostridium phytofermentans* cells dispersed therein.

FIG. 1 shows a fermentation vessel 10 that holds a medium 12 having a fermentable material dissolved or dispersed therein. The fermentable material is or includes a carbohydrate, e.g., glucose, cellobiose, or cellulose. The medium 12 also has a plurality of *Clostridium phytofermentans* cells 14 dispersed therein, such as $ISDg^T$ cells. The *Clostridium phytofermentans* cells 14 ferment the fermentable material to produce combustible fuel, e.g., ethanol and/or hydrogen. Other useful products and coproducts can also be produced.

Other products can include organic acids (e.g., formic acid, lactic acid and acetic acid), or their conjugate base (e.g., formate, lactate or acetate ions).

*Clostridium phytofermentans* cells 14 (American Type Culture Collection 700394$^T$) were isolated from damp silt in the bed of an intermittent stream in a forested site near Quabbin Reservoir in the state of Massachusetts (USA). Generally, ISDg$^T$ cells 14 are long, thin, straight, and motile rods (0.5 to 0.8 by 3.0 to 15.0 μm) that form round, terminal spores (0.9 to 1.5 μm in diameter). Additional characteristics of *Clostridium phytofermentans* cells are described in Warnick et al., *Int. J. Systematic and Evol. Microbiology*, 52, 1155-1160 (2002).

*Clostridium phytofermentans* cells 14 are cultured in an anaerobic environment, which is achieved and/or maintained by bubbling a substantially oxygen-free gas through a bubbler 16 that includes gas outlets 18 that are submerged below a surface 19 of the medium 12. Excess gas and effluent from reactions in the medium 12 fill headspace 22, and are eventually vented through a gas outlet aperture 21 formed in vessel wall 30. Gases that can be used to maintain anaerobic conditions include $N_2$, $N_2/CO_2$ (80:20), $N_2/CO_2/H_2$ (83:10:7), and Nobel gases, e.g., helium and argon. In some implementations, to achieve and/or maintain homogeneity, medium 12 is stirred (as indicated by arrow 40). Homogeneity can also be maintained by shaking or vibrating vessel 10.

In some instances, the concentration of *Clostridium phytofermentans* cells 14 suspended in the medium 12 is from about $10^6$ to about $10^9$ cells/mL, e.g., from about $10^7$ to about $10^8$ cells/mL. In some implementations, the concentration at the start of fermentation is about $10^7$ cells/mL.

We have found that *Clostridium phytofermentans* cells 14 can ferment both low, e.g., 0.01 mM to about 5 mM, and high concentrations of carbohydrates, and are generally not inhibited in their action at relatively high concentrations of carbohydrates, which would have adverse effects on other organisms. For example, the concentration of the carbohydrate in the medium can be greater than 20 mM, e.g., greater than 25 mM, 30 mM, 40 mM, 50 mM, 60 mM, 75 mM, 100 mM, 150 mM, 200 mM, 250 mM, 300 mM, or even greater than 500 mM or more. In any of these embodiments, the concentration of the carbohydrate is generally less than 2,000 mM.

The fermentable material can be, or can include, one or more low molecular weight carbohydrates. The low molecular weight carbohydrate can be, e.g., a monosaccharide, a disaccharide, an oligiosaccharide, or mixtures of these. The monosaccharide can be, e.g., a triose, a tetrose, a pentose, a hexose, a heptose, a nonose, or mixtures of these. For example, the monosaccharide can be arabinose, glyceraldehyde, dihydroxyacetone, erythrose, ribose, ribulose, xylose, glucose, galactose, mannose, fucose, fructose, sedoheptulose, neuraminic acid, or mixtures of these. The disaccharide can be, e.g., sucrose, lactose, maltose, gentiobiose, or mixtures of these.

In some embodiments, the low molecular weight carbohydrate is generated by breaking down a high molecular weight polysaccharides (e.g., cellulose, xylan or other components of hemicellulose, pectin, and/or starch). This technique can be advantageously and directly applied to waste streams, e.g., waste paper (e.g., waste newsprint and waste cartons). In some instances, the breaking down is done as a separate process, and then the low molecular weight carbohydrate utilized. In other instances, the high molecular weight carbohydrate is added directly to the medium, and is broken down into the low molecular weight carbohydrate in-situ. In some implementations, this is done chemically, e.g., by oxidation, base hydrolysis, and/or acid hydrolysis. Chemical hydrolysis has been described by Bjerre, *Biotechnol. Bioeng.*, 49:568, 1996, and Kim et al., *Biotechnol. Prog.*, 18:489, 2002.

In some implementations, the low molecular weight carbohydrate is generated by breaking down a polysaccharide using an enzyme or enzymes, e.g., endoglucanases, exoglucanases or cellobiohydrolases (CBH). These enzymes can be added to the polysaccharide source as enzyme preparations, or they may be made in-situ by an organism, e.g., *Aspergillus niger* BKMF 1305, and *Trichoderma reesei* RUT C30. Enzymatic breakdown has been discussed by T. Juhasz, *Food Tech. Biotechnol.* (2003), 41, 49.

In a specific implementation, lactose is used as the carbohydrate. Lactose is produced in large quantities by the cheese industry. For example, it has been estimated by Elliott, *Proceedings of the 38$^{th}$ Annual Marschall Cheese Seminar* (2001), that about 470 million pounds of lactose per year are produced by the U.S. cheese industry, and another 726 million pounds are produced in Europe. Lactose may be used in a fermentor, e.g., a seed fermentor that feeds a main fermentor, as a growth substrate for *Clostridium phytofermentans* cells alone, or along with other growth substrates. Lactose may be added to fermentation vessels to augment fermentation of low molecular weight carbohydrates and/or speed the decomposition and fermentation of cellulose, or other high molecular weight carbohydrates.

The fermentable material can also be, or can include one or more high molecular weight carbohydrates. High molecular weight carbohydrates include, e.g., polygalacturonic acid, cellulose, microcrystalline cellulose, pectin, starch, xylan, other hemicellulosic polymers, or mixtures of these. Microcrystalline cellulose and modified microcrystalline celluloses are available commercially from FMC Biopolymer under the trade name AVICEL®.

The fermentable material can also be, or can include, one or more biomass materials, e.g., cellulosic or lignocellulosic materials. Cellulosic materials are those materials that include cellulose, but substantially no lignin, e.g., less than 0.5 percent by weight. The cellulosic materials can be natural, semi-synthetic, or fully synthetic. For example, cotton is a natural cellulosic material. Semi-synthetic cellulosic materials include, e.g., rayon (regenerated cellulose) and textiles which include cotton fibers, e.g., obtained from virgin scrap textile materials (e.g., remnants), or post consumer waste, e.g., rags. Other semi-synthetic cellulosic materials include distillers grains (e.g., from the corn ethanol industry), paper and products such as polycoated paper and Kraft paper. The paper or paper products can be virgin materials, or they can be post-consumer waste materials.

Lignocellulosic materials include cellulose and a percentage of lignin, e.g., at least about 0.5 percent by weight to about 60 percent by weight or more lignin. Lignin can be thought of as a polyphenolic material. Some lignins can be represented by Structure (I) below:

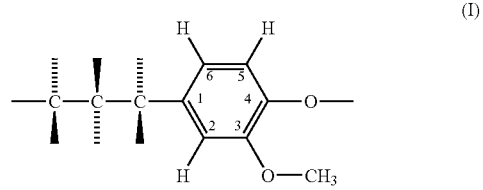

Lignins can be highly branched, and can also be partially crosslinked. Lignins can have significant structural variation that depends, at least in part, upon its source, e.g., whether it is derived from a softwood, or a hardwood.

Lignocellulosic materials include, e.g., papermaking sludge; wood, and wood-related materials, e.g., saw dust, particle board or leaves; and natural fiber sources, e.g., trees such as poplar trees, grasses such as switchgrass, leaves, grass clippings, rice hulls, bagasse, jute, hemp, flax, bamboo, sisal, abaca, straw, corn cobs, corn stover, wheat straw, rice hulls, and coconut hair.

In particular implementations, the lignocellulosic material is obtained from trees, such as Coniferous trees, e.g., Eastern Hemlock (*Tsuga canadensis*), Maidenhair Tree (*Ginkgo bilboa*), Pencil Cedar (*Juniperus virgineana*), Mountain Pine (*Pinus mugo*), Deodar (*Cedrus deodara*), Western Red Cedar (*Thuja plicata*), Common Yew (*Taxus baccata*), Colorado Spruce (*Picea pungens*); or Deciduous trees, e.g., Mountain Ash (*Sorbus*), Gum (*Eucalyptus gunnii*), Birch (*Betula platyphylla*), or Norway Maple (*Acer platanoides*), can be utilized. Poplar, Beech, Sugar Maple and Oak trees may also be utilized.

In some instances, *Clostridium phytofermentans* cells can ferment lignocellulosic materials directly without the need to remove lignin.

However, in certain embodiments, it is useful to remove at least some of the lignin from lignocellulosic materials before fermenting. For example, removal of the lignin from the lignocellulosic materials can make the remaining cellulosic material more porous and higher in surface area, which can, e.g., increase the rate of fermentation and ethanol yield. The lignin can be removed from lignocellulosic materials, e.g., by sulfite processes, alkaline processes, or by Kraft processes. Such process and others are described in Meister, U.S. Pat. No. 5,138,007, and Knauf et al., *International Sugar Journal*, 106:1263, 147-150 (2004). The lignin content of switchgrass is about 17.6% (percent dry weight), which is about the same as corn stover. The lignin content of writing paper ranges from about zero percent lignin to about 12 percent lignin. Some office papers have a lignin content that is in the range of about 11-12 percent lignin. Mosier et al., *Bioresource Technology* 96:673, 2005, discusses the lignin content of some materials, and also some pretreatment strategies for removing it. If lignin is removed, it can be used as an energy source in the processes, e.g., to heat a boiler by burning the lignin.

Cellulosic materials can be obtained from lignocellulosic materials by chemically treating the lignocellulosic material to solubilize the lignin to a degree that allows the cellulosic material to be separated for the lignin, e.g., in the form of fibers. When the lignocellulosic material is from trees, the dissolved lignin generally constitutes between about 25 to 45% of the material.

Materials can be reduced in size, e.g., by shearing the material in a rotary knife cutter, or by pulverizing the material in a ball mill. When a rotary knife cutter is used to reduce the size of the material, e.g., a cellulosic or lignocellulosic material, typically the resulting material is fibrous in nature, having a substantial length-to-diameter ratio, e.g., greater than 5/1, greater than 10/1, greater than 15/1, greater than 20/1, or even greater than 25/1. When a ball-mill is used, typically the resulting material is in the form of flour, typically having substantially spherical particles, e.g., having a diameter of less than 5 microns, e.g., less than 4, less than 2.5, less than 1 micron.

Figure 2:
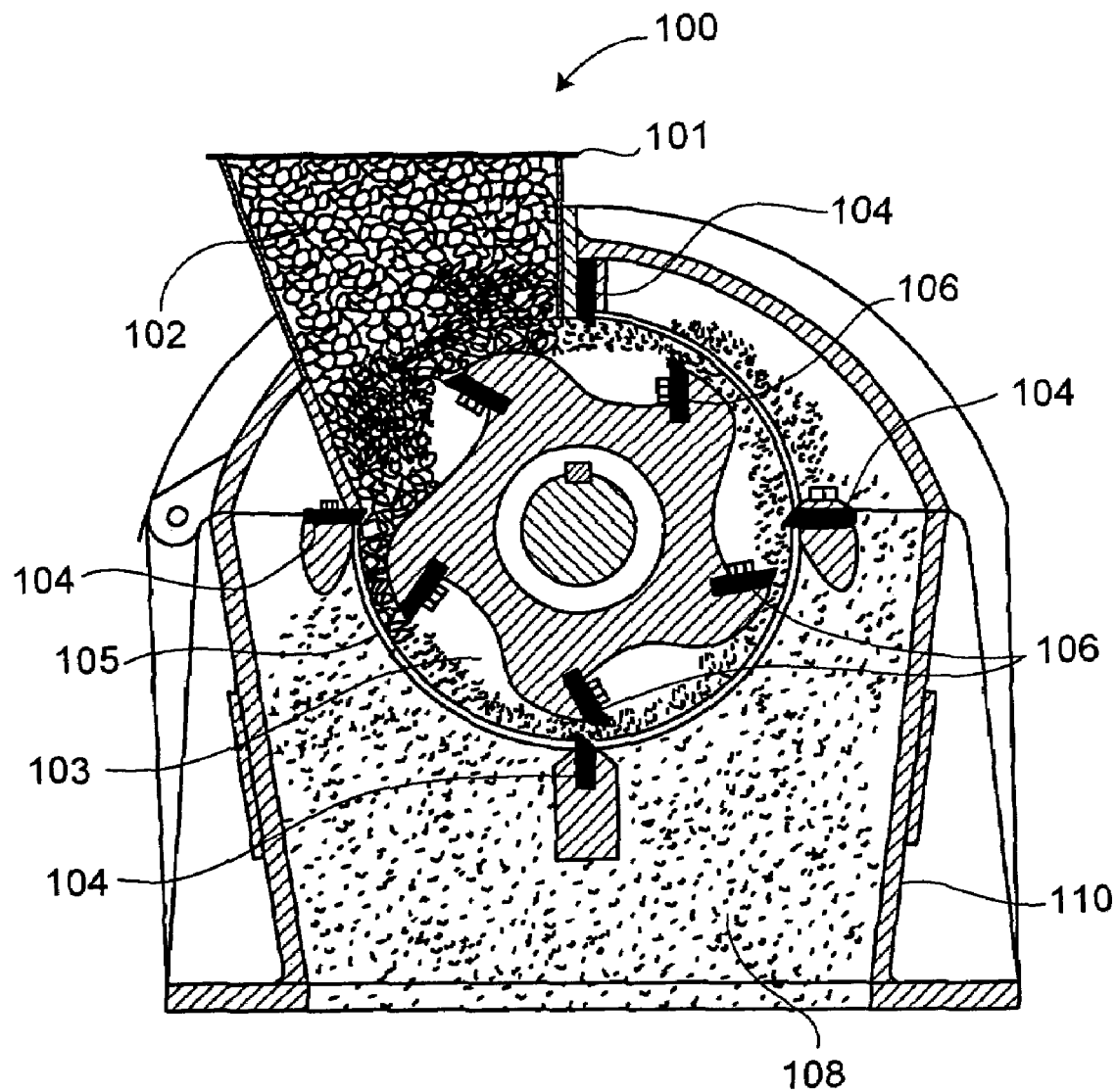
FIG. 2 is a schematic cross-sectional view of a rotary knife cutter used to fibrillate biomass.
Figure 3A:
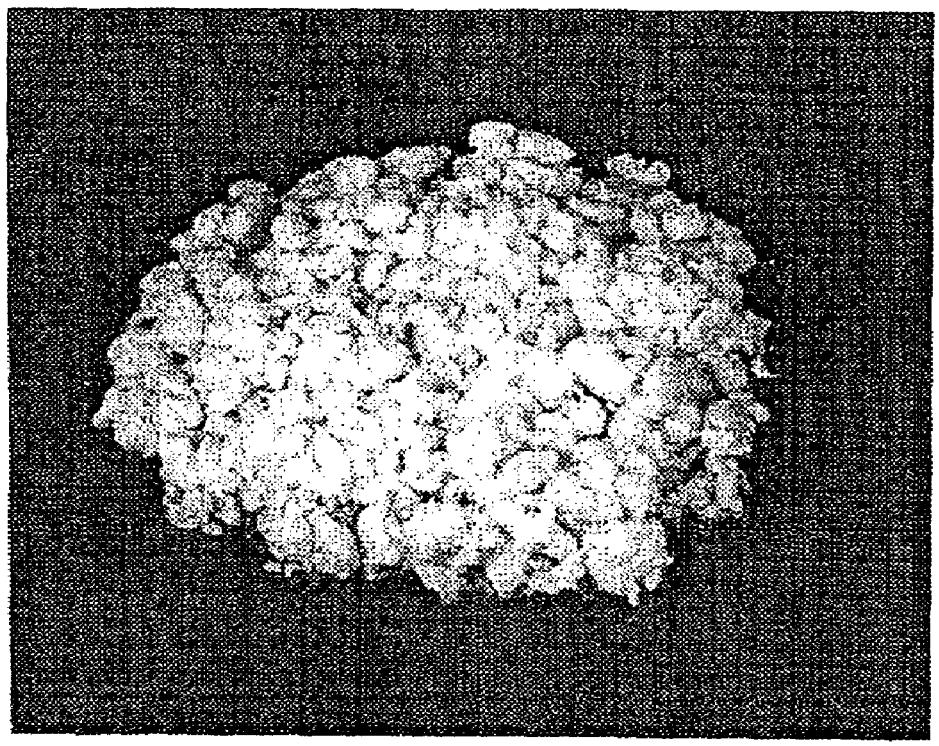
FIG. 3A is a photograph of cellulosic material sheared in the rotary knife cutter of FIG. 2.
Figure 3B:
FIG. 3B is highly enlarged photomicrograph of the material shown in FIG. 3A.

FIG. 2 shows a rotary knife cutter 100 that includes a hopper 101 that can be loaded with a cellulosic or lignocellulosic material 102, e.g., in the form of chips. The cellulosic or lignocellulosic material is drawn into a shearing zone 103, and is sheared between stationary blades 104 and rotating blades 106. A screen 105 prevents the cellulosic or lignocellulosic material from leaving the shearing zone 103 until the material is sized small enough to pass through apertures defined in the screen. Once the cellulosic or lignocellulosic material has passed through openings in the screen, it is captured in bin 110. To aid in the collection of the sheared fibrous cellulosic or lignocellulosic material, bin 110 can be maintained at a pressure below nominal atmospheric pressure. The fibrous cellulosic or lignocellulosic material collected in the bin has a relatively low bulk density, e.g., less than 0.5 grams per cubic centimeter, e.g., less than 0.3 grams per cubic centimeter, or even less than 0.2 grams per cubic centimeter, and has a "fluffy" appearance, as shown in FIGS. 3A and 3B.

In some implementations, it can be desirable to use a fibrous material that has a relatively high surface area and/or a relatively high porosity. For example, a desirable fibrous material can have a surface area of greater than 0.5 $m^2/g$, e.g., greater than 1.0 $m^2/g$, 1.5 $m^2/g$, 1.75 $m^2/g$, 5 $m^2/g$, or even greater than 10 $m^2/g$, as measured using BET Brunauer Emmett Teller surface area measurements); and/or a porosity of greater than 70 percent, e.g., greater than 80 percent, 87.5 percent, 90 percent, or even greater than 95 percent, as determined mercury porosimetry. High surface areas and/or high porosities can increase hydrolysis rate and/or fermentation rate.

Blends of any of the above materials can be used, e.g., blends of materials obtained from paper sources, and materials obtained from cotton.

In some embodiments, fermentors that include a medium that includes *Clostridium phytofermentans* dispersed therein are configured to continuously remove a fermentation product, such as ethanol. In some embodiments, the concentration of the desired product remains substantially constant, or within about twenty five percent of an average concentration, e.g., measured after 2, 3, 4, 5, 6, or 10 hours of fermentation at an initial concentration of from about 10 mM to about 25 mM. In some embodiments, any biomass material or mixture described herein is continuously fed to the fermentors.

The medium for *Clostridium phytofermentans* can include additional constituents, such as buffers, e.g., $NaHCO_3$, $NH_4Cl$, $NaH_2PO_4.H_2O$, $K_2HPO_4$, and $KH_2PO_4$; electrolytes, e.g., KCl, and NaCl; growth factors; surfactants; and chelating agents. Growth factors include, e.g., biotin, folic acid, pyridoxine.HCl, riboflavin, urea, yeast extracts, thymine, tryptone, adenine, cytosine, guanosine, uracil, nicotinic acid, pantothenic acid, B12 (Cyanocobalamine), p-aminobenzoic acid, and thioctic acid. Minerals include, e.g., $MgSO_4$, $MnSO_4.H_2O$, $FeSO_4.7H_2O$, $CaCl_2.2H_2O$, $CoCl_2.6H_2O$, $ZnCl_2$, $CuSO_4.5H_2O$, $AlK(SO_4)_2.12H_2O$, $H_3BO_3$, $Na_2MoO_4$, $NiCl_2.6H_2O$, and $NaWO_4.2H_2O$. Chelating agents include, e.g., nitrilotriacetic acid. Surfactants include, e.g., polyethylene glycol (PEG), polypropylene glycol (PPG), copolymers PEG and PPG and polyvinylalcohol.

In some implementations, fermentation conditions include maintaining the medium at a temperature of less than about 45° C., e.g., less than about 42° C. (e.g., between about 34° C. and 38° C., or about 37° C.). In any of these implementations, generally, the medium is maintained at a temperature above about 5° C., e.g., above about 15° C.

In some implementations, fermentation conditions include maintaining the medium at a pH of below about 9.5, e.g., between about 6.0 and 9.0, or between about 8 and 8.5. Generally, during fermentation, the pH of the medium typically does not change by more than 1.5 pH units. For example, if the fermentation starts at a pH of about 7.5, it typically does not go lower than pH 6.0 at the end of the fermentation, which is within the growth range of the cells.

*Clostridium phytofermentans* cells adapt to relatively high concentrations of ethanol, e.g., 7 percent by weight or higher, e.g., 12.5 percent by weight. *Clostridium phytofermentans* cells can be grown in an ethanol rich environment prior to fermentation, e.g., 7 percent ethanol, to adapt the cells to even higher concentrations of ethanol, e.g., 20 percent. In some embodiments, *Clostridium phytofermentans* is adapted in successively higher concentrations of ethanol, e.g., starting with 2 percent ethanol, then 5 percent ethanol, and then 10 percent ethanol.

Products in addition to or other than ethanol can be produced. More generally, fermentation products include fuels, such as alcohols (e.g., ethanol, n-propanol, isopropanol, n-butanol, or mixtures of these) and hydrogen. Other products include organic acids (e.g., formic acid, lactic acid, acetic acid or mixtures of these), or their conjugate bases (e.g., formate, lactate or acetate ions) or salts thereof.

*Clostridium phytofermentans*, such as strain ISDg$^T$, can be used alone or in combination with one or more other microbes, such as yeasts or fungi (e.g., *Saccharomyces cerevisiae, Pichia stipitis, Trichoderma* species, *Aspergillus* species) or other bacteria (e.g., *Zymomonas mobilis, Klebsiella oxytoca, Escherichia coli, Clostridium acetobutylicum, Clostridium beijerinckii, Clostridium papyrosolvens, Clostridium cellulolyticum, Clostridium josui, Clostridium termitidis, Clostridium cellulose, Clostridium celerecrescens, Clostridium populeti, Clostridium cellulovorans*). For example, when a cellulolytic clostridium (strain C7) was grown in coculture with *Zymomonas mobilis* in a medium containing cellulose as the growth substrate, ethanol yields were 2.5-fold higher than in cultures with the clostridium alone (Leschine and Canale-Parola, *Current Microbiology*, 11:129-136, 1984). Mixtures of microbes can be provided as solid mixtures (e.g., freeze-dried mixtures), or as liquid dispersions of the microbes, and grown in coculture with *Clostridium phytofermentans*, or microbes may be added sequentially to the culture medium, for example, by adding another microbe before or after addition of *Clostridium phytofermentans*.

In addition, any of the biomass materials described herein or mixtures of any of the biomass materials described herein can be treated with one or more microbes described herein in a sequential or concurrent manner. For example, the biomass (or biomass mixture) can be treated concurrently with a mixture of microbes, e.g., a coculture, or the biomass (or biomass mixture) can be initially treated with a first microbe or a first mixture of microbes (e.g., one or more yeasts, fungi or other bacteria) and then the resulting biomass can be treated with one or more stains of *Clostridium phytofermentans*. In other embodiments, the biomass material (or biomass mixture) is initially treated with one or more stains of *Clostridium phytofermentans* and then the resulting biomass is treated with one or more other microbes (any one of or mixtures of microbes described herein).

Large Scale Ethanol Production from Biomass

Generally, there are two basic approaches to producing fuel grade ethanol from biomass on a large scale utilizing of *Clostridium phytofermentans* cells. In the first method, one first hydrolyzes a biomass material that includes high molecular weight carbohydrates to lower molecular weight carbohydrates, and then ferments the lower molecular weight carbohydrates utilizing of *Clostridium phytofermentans* cells to produce ethanol. In the second method, one ferments the biomass material itself without chemical and/or enzymatic pretreatment. In the first method, hydrolysis can be accomplished using acids, e.g., Brönsted acids (e.g., sulfuric or hydrochloric acid), bases, e.g., sodium hydroxide, hydrothermal processes, ammonia fiber explosion processes ("EFEX"), lime processes, enzymes, or combination of these. Hydrogen, and other products of the fermentation can be captured and purified if desired, or disposed of, e.g., by burning. For example, the hydrogen gas can be flared, or used as an energy source in the process, e.g., to drive a steam boiler, e.g., by burning. Hydrolysis and/or steam treatment of the biomass can, e.g., increase porosity and/or surface area of the biomass, often leaving the cellulosic materials more exposed to *Clostridium phytofermentans* cells, which can increase fermentation rate and yield. Removal of lignin can, e.g., provide a combustible fuel for driving a boiler, and can also, e.g., increase porosity and/or surface area of the biomass, often increasing fermentation rate and yield. Generally, in any of the below described embodiments, the initial concentration of the carbohydrates in the medium is greater than 20 mM, e.g., greater than 30 mM, 50 mM, 75 mM, 100 mM, 150 mM, 200 mM, or even greater than 500 mM.

Ethanol Production From Biomass Utilizing Acid Hydrolysis Pretreatment

Figure 4:
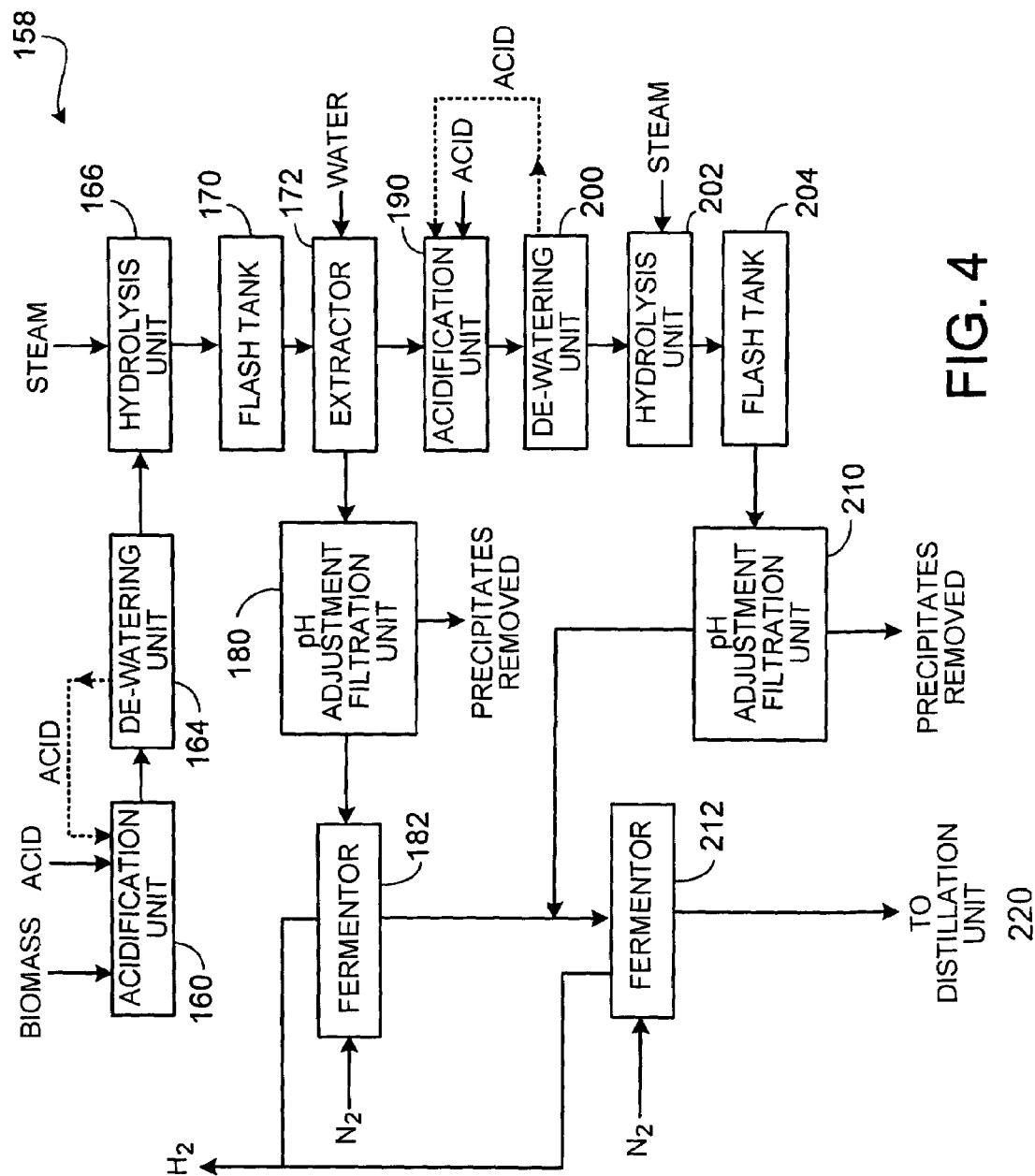
FIG. 4 is a block diagram that shows a process for producing ethanol and hydrogen from biomass using acid hydrolysis pretreatment.

FIG. 4 illustrates a process 158 for producing ethanol from biomass by first treating biomass (e.g., between about 10 and about 60 weight percent) suspended in water with an acid in an acidification unit 160. The biomass can be, e.g., wood chips, sawdust, milled agricultural residues or biomass crops (e.g., corn stover or switchgrass), corn-refining residue, sheared paper products like those shown in FIGS. 3A and 3B, or mixtures of these and other cellulosic and/or lignocellulosic materials. The biomass can be acidified by bubbling gaseous sulfur dioxide through the biomass that is suspended in the water, or by adding a strong acid, e.g., sulfuric, hydrochloric, or nitric acid. During the acidification, the pH is maintained at below about 3, e.g., below about 2.5 or below about 1.5. In addition to the acid already in the acidification unit, optionally, a metal salt such as ferrous sulfate, ferric sulfate, ferric chloride, aluminum sulfate, aluminum chloride, magnesium sulfate, or mixtures of these can be added to aid in the hydrolysis of the biomass. The biomass is held in the acidification unit 160, e.g., between about 1 and 6 hours, at a temperature of, e.g., between about 40° C. and about 80° C.

After acidification in the acidification unit 160, the biomass is de-watered in de-watering unit 164, e.g., by squeezing or by centrifugation, to remove much of the acidified water. If desired, the acidified water can be re-used in the acidification unit 160.

The acid-impregnated biomass is fed into a hydrolysis unit 166, e.g., by a gravity feeder or rotary valve feeder that, in some instances, does not substantially densify the biomass. Steam is injected into the hydrolysis unit 166 to directly contact and heat the biomass to the desired temperature. The temperature of the steam is, e.g., between about 130° C. and about 220° C., and steam injection is continued for a time, e.g., of between about 10 minutes and about 120 minutes. The hydrolysate is then discharged into flash tank 170 operating at a temperature of, e.g., between about 100° C. and about 190° C., and is held in the tank 170 for a period of time, e.g., between about 1 hour and about 6 hours, to further hydrolyze the biomass, e.g., into soluble oligosaccharides and monomeric sugars.

The hydrolysate is then fed into extractor 172, e.g., a countercurrent extractor, a screw-conveyor extractor, or a vacuum belt extractor. In extractor 172, the hydrolysate is washed with hot water at a temperature of, e.g., between about 40° C.

to about 90° C. For example, the hydrolysate is washed with a quantity of water greater than its own weight, e.g., greater than two times its own weight, e.g., three times, four times, eight times, or even greater than ten times its own weight.

Alkali, e.g., in the form of lime or ammonia, is added to the extract in the pH adjustment and filtration unit 180 to adjust the pH of the extract to between about 7 and about 8. Any precipitates during the addition of the alkali are removed and the filtrate is forwarded to a fermentor 182, which holds a medium that has *Clostridium phytofermentans* cells dispersed therein. The initial concentration of the carbohydrates in the medium is between 20 mM and about 100 mM. The concentration of *Clostridium phytofermentans* cells suspended in the medium is, e.g., from about $10^7$ to about $10^9$ cells/mL. In one implementation, the medium (referred to as GS-2) contains (each expressed in g/L) yeast extract, 6.0; urea, 2.1; $K_2HPO_4$, 2.9; $KH_2PO_4$, 1.5; MOPS; 10.0; trisodium citrate dihydrate, 3.0; cysteine hydrochloride, 2.0. In other implementations, components may be added to, or substituted for the components in the GS-2 medium, including: Tryptone, 2.0; adenine, 0.02; cytosine, 0.05; guanosine, 0.02; thymine, 0.05; uracil, 0.04; and a quantity of a vitamin solution, e.g., 10 g/mL, prepared as described in Wolin et al., *Bacteriology*, 87:993, 1964. The extract from the pH and filtration unit 180 is adjusted so that the initial concentration of carbohydrates in the medium is, e.g., between about pH 7.0 and pH 7.5.

If desired, at the start of the fermentation, in addition to the hydrolysate, a low molecular weight carbohydrate, e.g., lactose, can be added to an initial concentration of, e.g., between about 1.0 g/L and 5 g/L. This can help rapidly increase the number of *Clostridium phytofermentans* cells and build enzymes within the fermentor. Fermentation is allowed to proceed while bubbling nitrogen gas through the medium for a period of time, e.g., between about 8 hours and 72 hours, while maintaining a temperature of, e.g., between about 15° C. and 40° C. Hydrogen gas produced during the fermentation is swept from fermentor 182 by the nitrogen gas, and is either collected or flared.

The extracted solids from the extractor 172 are de-watered, and then fed to second acidification unit 190. The solids from the extractor are soaked in an aqueous solution of an acid, and optionally, a metal salt. During the acidification, the pH is maintained at below about 3, e.g., below about 2.5 or below about 1.5. The biomass is held in the second acidification unit 190, e.g., between about 1 and 6 hours, at a temperature of, e.g., between about 40° C. and about 80° C.

After acidification in the acidification unit 190, the biomass is de-watered in de-watering unit 200, e.g., by squeezing or by centrifugation, to remove much of the acidified water. If desired, the acidified water can be re-used in the acidification unit 160 and/or acidification unit 190.

The acid-impregnated biomass is fed into second hydrolysis unit 202. Steam is injected into the second hydrolysis unit 202 to directly contact and heat the biomass to a desired temperature. The temperature of the steam and time of treatment is generally the same as used in the first hydrolysis unit 166. The hydrolysate is then discharged into a flash tank 204 operating at a temperature of, e.g., between about 140° C. and about 190° C., and is held in the tank 204 for a period of time, e.g., between about 0.5 and about 12 hours to further hydrolyze the biomass.

Alkali is added to the extract in the pH adjustment and filtration unit 210 to adjust the pH of the extract to between about 7 and about 8. Any precipitates during the addition of the alkali are removed, and the filtrate is combined with the contents of fermentor 182, and then forwarded to fermentor 212. Fermentation is allowed to proceed while bubbling nitrogen gas through the medium for a period of time, e.g., between about 15 hours and 100 hours, while maintaining a temperature of, e.g., between about 25° C. and 35° C. Hydrogen gas produced during the fermentation is swept from fermentor 212 by the nitrogen gas, and is either collected or flared.

After fermentation, the entire contents of fermentor 212 is transferred to distillation unit 220, and 96 percent ethanol/4 percent water (by volume) is distilled and collected. Fuel grade ethanol (99-100 percent ethanol) can be obtained by azeotropic distillation of the 96 percent ethanol, e.g., by the addition of benzene and then re-distilling the mixture, or by passing the 96 percent ethanol through molecular sieves to remove the water.

Ethanol Production From Biomass Utilizing Enzyme Hydrolysis Pretreatment

Figures 5A, 5B:
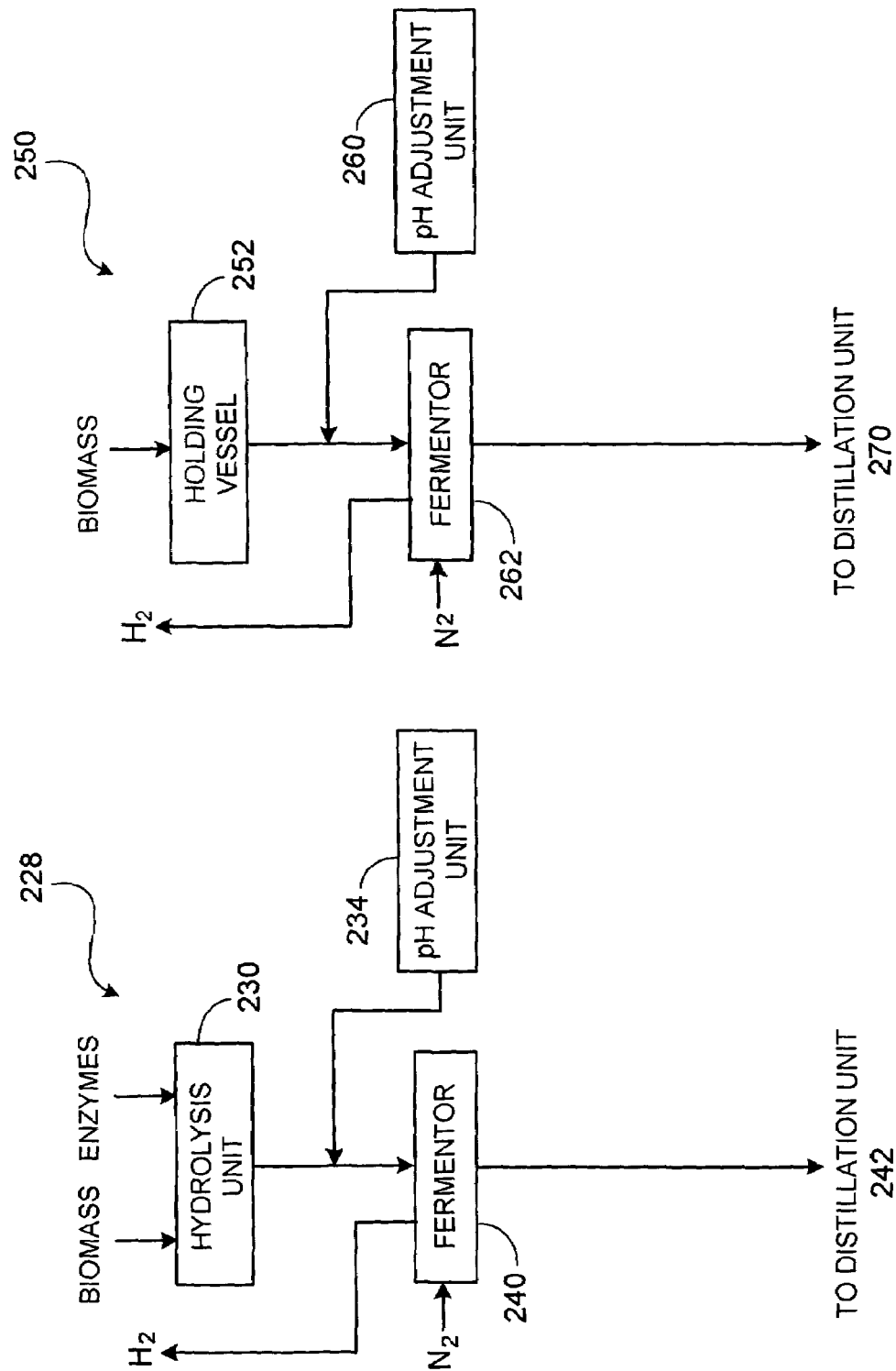
FIG. 5A is a block diagram that shows a process for producing ethanol and hydrogen from biomass using enzymatic hydrolysis pretreatment.
FIG. 5B is a block diagram that shows a process for producing ethanol and hydrogen from biomass using biomass that has not been enzymatically pretreated.

FIG. 5A illustrates a process 228 for producing ethanol from biomass by first treating biomass (between 10 and 60 weight percent), e.g., suspended in water, with an enzyme or mixture of enzymes, e.g., endoglucanases, exoglucanases, cellobiohydrolases (CBH), beta-glucosidases, glycoside hydrolases, glycosyltransferases, lyases, and esterases active against components of hemicellulsoe, pectin and starch, in a hydrolysis unit 230. During the hydrolysis, the pH is maintained between about 6.0 and about 7.5 by adding sodium hydroxide. The biomass is held in the hydrolysis unit 230, e.g., between about 6 and 120 hours, at a temperature of, e.g., between about 25° C. and about 40° C., and under nitrogen.

After hydrolysis, alkali, e.g., in the form of lime or ammonia, and/or acid, e.g., in the form of an aqueous solution of sulfuric acid, is added to the contents of the hydrolysis unit 230 via pH adjustment unit 234 to adjust the pH of the contents to between about 7 and about 8. After the pH is adjusted, the entire contents of hydrolysis unit 230 are transferred to fermentor 240, which holds a medium that has *Clostridium phytofermentans* cells dispersed therein. The initial concentration of the carbohydrates in the medium is between 20 mM and about 100 mM. The concentration of *Clostridium phytofermentans* cells suspended in the medium is, e.g., from about $10^7$ to about $10^9$ cells/mL. In one implementation, the medium contains (each expressed in g/L) yeast extract, 6.0, urea, 2.1, $K_2HPO_4$, 2.9; $KH_2PO_4$, 1.5; MOPS; 10.0; trisodium citrate dihydrate, 3.0; cysteine hydrochloride. The effluent from hydrolysis unit 230 is adjusted so that the initial concentration of carbohydrates in the medium is, e.g., between about 50 and 200 mM. If desired, at the start of the fermentation, cellobiose can be added to an initial concentration of, e.g., between about 1.0 g/L and 5 g/L, or lactose can be added to speed fermentation or hydrolysis. Fermentation is allowed to proceed while bubbling nitrogen gas through the medium for a period of time, e.g., between about 8 hours and 72 hours, while maintaining a temperature of, e.g., between about 15° C. and 40° C. Hydrogen gas produced during the fermentation is swept from fermentor 240 by the nitrogen gas, and is either collected or flared.

After fermentation, the entire contents of the fermentor 240 are transferred to distillation unit 242, and fuel grade ethanol can be obtained as discussed above.

Ethanol Production From Biomass Without Acid or Enzyme Pretreatment

FIG. 5B illustrates a process 250 for producing ethanol from biomass by first charging a holding vessel 252 with biomass, e.g., between 10 and 60 weight percent, suspended in water. The biomass may be allowed to soak for a time, e.g., of between about 1 hour and 36 hours at a temperature of, e.g., between about 25° C. and about 90° C. if under normal atmospheric pressure, or between about 100 to about 175 if under pressures higher than normal atmospheric pressure, e.g., between about 1.5 atmospheres and about 10 atmosphere. Alkali, e.g., in the form of lime or ammonia, and/or acid, e.g., in the form of an aqueous solution of sulfuric acid, is added to the contents of the holding vessel 252 after the soaking time via pH adjustment unit 260 to adjust the pH of the contents to between about 7 and about 8. After the pH is adjusted, the entire contents of the holding vessel 252 are transferred to fermentor 262, which holds a medium that has *Clostridium phytofermentans* cells dispersed therein. The initial concentration of the carbohydrates in the medium is between 20 mM and about 100 mM. Fermentation occurs in fermentation vessel 262 under conditions that have been described above. Fuel grade ethanol is distilled in distillation unit 270, also as described above.

Figure 5C:
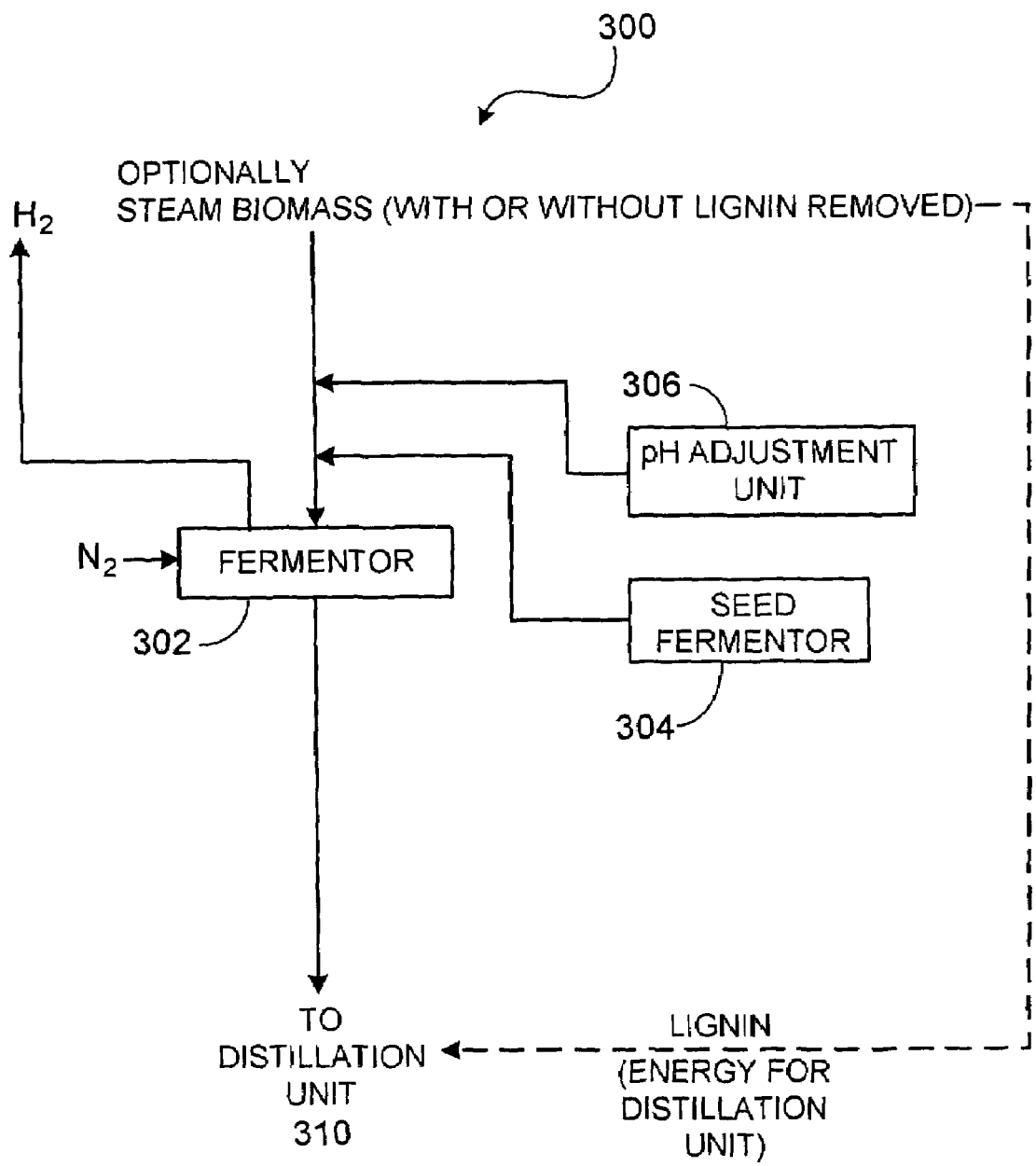
FIG. 5C is a block diagram that shows a process for producing ethanol and hydrogen from biomass using biomass that has not been chemically or enzymatically pretreated, but is optionally steam treated.

FIG. 5C illustrates a process 300 for producing ethanol from biomass. Biomass (with or without lignin removed), and, optionally, steam is charged to a fermentor 302. If lignin is removed, it can be used in any energy intensive process such as energy to drive a distillation unit. Steam can be advantageous to sterilize the biomass, and also to loosen the biomass and make it more reactive. The biomass is charged to the fermentor 302 and water is added (if necessary) so that, e.g., between about 10 and 60 weight percent of the total mass is suspended biomass. The biomass may be allowed to soak for a time, e.g., between about 1 hour and 36 hours, at a temperature of, e.g., between about 25° C. and about 90° C. if under normal atmospheric pressure, or between about 100° C. to about 175° C. if under pressures higher than normal atmospheric pressure, e.g., between about 1.5 atmospheres and about 10 atmosphere. Alkali, e.g., in the form of lime or ammonia, and/or acid, e.g., in the form of an aqueous solution of sulfuric acid, is added to the contents of the fermentor 302 after the soaking time via pH adjustment unit 306 to adjust the pH of the contents to between about 7 and about 8.

Seed fermentor 304, which holds a medium that has *Clostridium phytofermentans* cells dispersed therein, is used to grow the *Clostridium phytofermentans* cells. The concentration of *Clostridium phytofermentans* cells suspended in the medium is, e.g., about $10^7$ at the start of growth, and about $10^8$ cells/mL when the seed mixture is ready for use to ferment carbohydrates. The initial concentration of the carbohydrates in the medium is between 20 mM and about 100 mM. In one implementation, the medium contains (each expressed in g/L) yeast extract, 6.0, urea, 2.1, $K_2HPO_4$, 2.9; $KH_2PO_4$, 1.5; MOPS; 10.0; trisodium citrate dihydrate, 3.0; and cysteine hydrochloride. The entire contents of the seed fermentor 304 is transferred to fermentor 302 held at about room temperature, and allowed to ferment under conditions that have been described above. Fuel grade ethanol is distilled in distillation unit 270, also as described above.

Ethanol Production From Biomass Utilizing a Combination of Acid Hydrolysis Pretreatment, and Enzyme Hydrolysis Pretreatment Ethanol from biomass can also be produced using a combination of acid hydrolysis pretreatment and enzyme hydrolysis pretreatment. For example, an initial hydrolysis can take place using an acid, e.g., by treatment of the biomass in an acidification unit, followed by steam injection (as shown in FIG. 4), and then a final hydrolysis can be applied to the initially hydrolyzed biomass using enzyme hydrolysis (as shown in FIG. 5A).

Any combination of the ethanol production methods and/or features can be utilized to make a hybrid production method. In any of the methods described herein, lignin can be removed before fermentation. Furthermore, products in addition to or other than ethanol can be produced by any of the methods described herein. More generally, fermentation products include fuels, such as alcohols and hydrogen, and other products, such as organic acids. *Clostridium phytofermentans*, such as strain $ISDg^T$, can be used alone, or synergistically in combination with one or more of any of the other microbes (e.g., yeasts or other bacteria) described herein.

EXAMPLES

The disclosure is further described in the following examples, which do not limit the scope of the invention described in the claims.

In one experiment, *Clostridium phytofermentans* was grown in culture tubes in GS-2 cellulose medium at an initial pH of 7.5 under an atmosphere of $N_2$. The initial *Clostridium phytofermentans* concentration was about $0.8$-$1.1 \times 10^7$ cells/mL and the temperature of incubation was 30° C.

Figure 6:
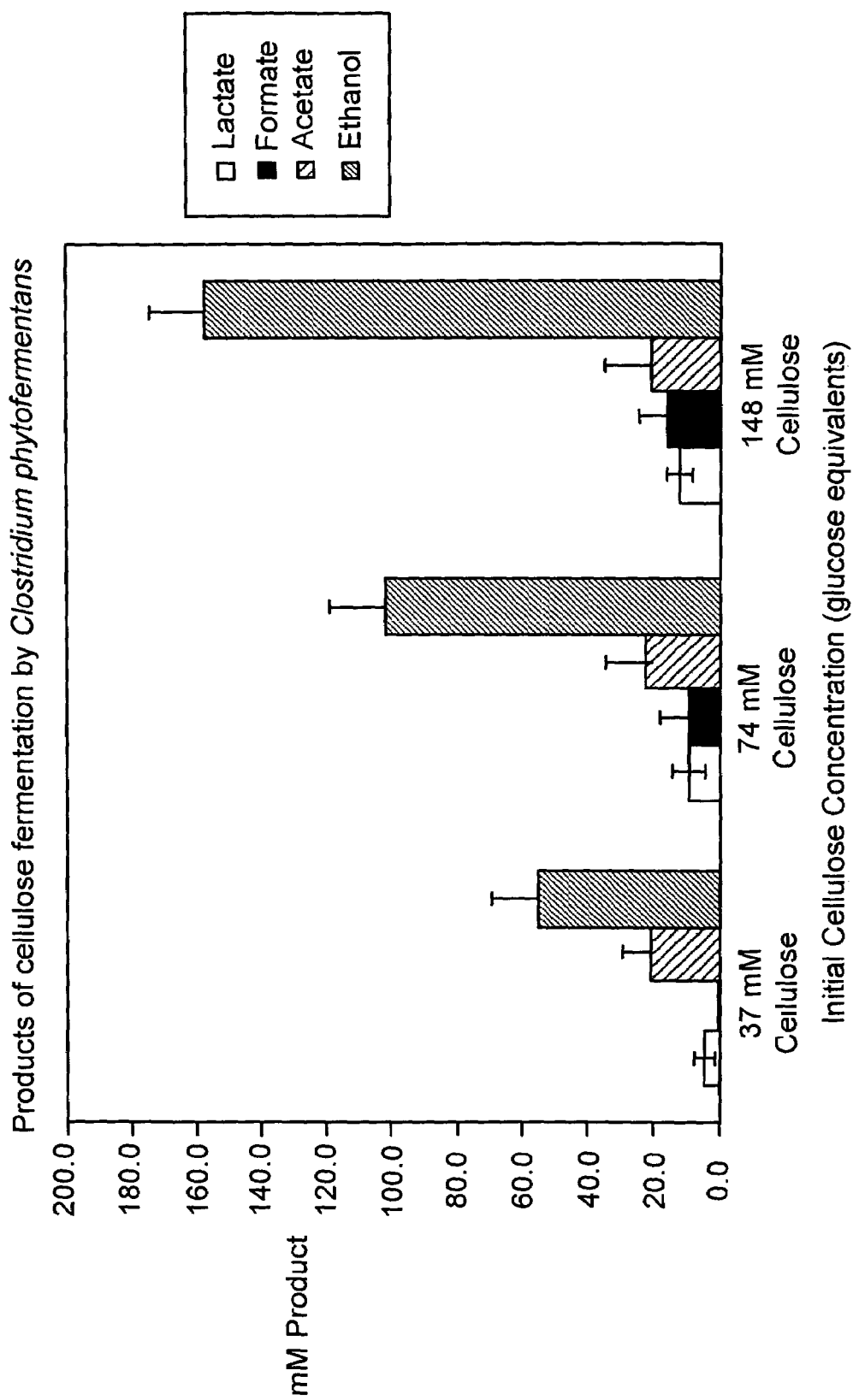
FIG. 6 is a bar chart that shows major products and concentrations of the products obtained from fermenting various initial cellulose concentrations (in glucose equivalents) together with *Clostridium phytofermentans*.

FIG. 6 shows the concentration of ethanol (E), acetate (A), formate (F), and lactate (L) upon completion of cellulose decomposition as a function of initial cellulose concentration (in glucose equivalents). At an initial cellulose concentration of 37 mM, the concentrations of lactate (L), acetate (A), and ethanol (E), were 4 mM, 20 mM, and 59 mM, respectively. Formate (F) was not detectable at this initial concentration. At an initial cellulose concentration of 74 mM, the concentrations of lactate (L), formate (F), acetate (A), and ethanol (E), were 7 mM, 10 mM, 20 mM, and 123 mM, respectively; and at a concentration of 148 mM, the concentrations of lactate (L), formate (F), acetate (A), and ethanol (E), were 10 mM, 17 mM, 20 mM, and 160 mM, respectively. FIG. 6 shows that high concentrations of cellulose do not inhibit the action of *Clostridium phytofermentans*, since the concentration of ethanol (E) increases with increasing initial concentration of cellulose.

This result contrasts with the results obtained using other cellulose-fermenting microbes that do not ferment higher concentrations of cellulose, e.g., above about 40 mM (in glucose equivalents), and produce decreased amounts of ethanol at higher cellulose concentrations (see Desvaux et al., *Appl. Environ. Microbiology*, 66, 2461-2470, 2000). It is also notable that when using *Clostridium phytofermentans* the acetate levels do not significantly increase with increasing initial concentration of cellulose, which can be advantageous because more of the cellulose goes into making the more economically valuable ethanol. Generally, other cellulolytic bacteria produce less ethanol than acetate (on a molar basis) and ethanol-to-acetate ratios decrease with increasing initial cellulose concentrations (for example, see Desvaux et al. above).

In a second experiment, *Clostridium phytofermentans* was grown in culture tubes in GS-2 medium containing cellulose at 25 or 50 mM (glucose equivalents), or xylan at 25 or 50 mM (xylose equivalents), or cellulose plus xylan, each at 25 or 50 mM, for a total carbohydrate concentration of 50 or 100 mM (monosaccharide equivalents). The initial pH of media was 7.5 and the initial *Clostridium phytofermentans* concentration was $0.8$-$1.1 \times 10^7$ cells/mL Cultures were incubated under an atmosphere of $N_2$ at 30° C. Carbohydrate degradation was monitored visually.

In cultures containing both carbohydrates, cellulose and xylan were degraded simultaneously. The rate of decomposition of cellulose or xylan in cultures containing both carbohydrates was equal to or greater than the rate of decomposition in cultures containing a single carbohydrate. This experiment demonstrates that the fermentation of cellulose by cultures of *Clostridium phytofermentans* is not inhibited by xylan, a five-carbon sugar polymer, and an important component of hemicellulose. Furthermore, this experiment shows that cellulose and xylan are fermented simultaneously by cultures of *Clostridium phytofermentans*, which can be advantageous given that most natural sources of biomass contain mixtures of carbohydrates, with cellulose as the most abundant component and hemicelluloses, such as xylan, second in abundance only to cellulose. In contrast, it appears that other microbes cannot ferment the 5-carbon sugars, or polymers that include 5-carbon sugar repeat units. Also, with other microbes, the 5-carbon sugars, or polymers thereof, can actually interfere with metabolic processes of the microbes to reduce fermentation rate and yield of ethanol.

In a third experiment, *Clostridium phytofermentans* was grown in culture tubes in GS-2 medium containing starch (Difco soluble starch) at 10, 20, or 40 g/L. The initial pH of media was 7.5 and the initial *Clostridium phytofermentans* concentration was $0.8-1.1 \times 10^7$ cells/mL. Cultures were incubated under an atmosphere of $N_2$ at 30° C. Starch fermentation was indicated by gas production and an increase in culture turbidity. Upon completion of fermentation, the concentrations of fermentation products were determined. At an initial starch concentration of 10 g/L, the concentrations of lactate, formate, acetate, and ethanol, were 1 mM, 2 mM, 4 mM, and 69 mM, respectively. At an initial starch concentration of 20 g/L, the concentrations of lactate, formate, acetate, and ethanol, were 3 mM, 4 mM, 5 mM, and 127 mM, respectively. At an initial starch concentration of 40 g/L, the concentrations of lactate, acetate, and ethanol, were 11 mM, 4 mM, and 132 mM, respectively. Formate was not detected in this later experiment. These experiments indicate that higher concentrations of starch do not inhibit the action of *Clostridium phytofermentans*, since the concentration of ethanol increases with increasing initial concentration of starch, a result analogous to that described above where cells were cultured with increasing concentrations of cellulose.

In a fourth experiment, *Clostridium phytofermentans* was grown in culture tubes in GS-2 medium containing ground corn at 27 g/L, or wet distillers grains at 10.5 g/L, or shredded corn stover at 20 g/L, or shredded switch grass at 20 g/L. The initial pH of media was 7.5 and the initial *Clostridium phytofermentans* concentration was $0.8-1.1 \times 10^7$ cells/mL. Cultures were incubated under an atmosphere of $N_2$ at 30° C. All substrates were fermented, as indicated by gas production, and the primary fermentation product in all cultures was ethanol. This experiment indicates that *Clostridium phytofermentans* ferments these cellulosic feedstocks to ethanol without chemical pretreatment of the cellulosic feedstock and without the addition of cellulases or other enzymes.

In a final example, analyses of the genome sequence of *Clostridium phytofermentans* support the conclusion that this microbe possesses unusual fermentation properties, and is particularly well suited to decomposing multiple components of plant biomass and fermenting these components to ethanol. The genome of *Clostridium phytofermentans* has been sequenced by the Joint Genome Institute of the U.S. Department of Energy. A draft sequence assembly was first available Nov. 8, 2005 and was released to the public May 20, 2006 (http://genome.onl.gov/microbial/cphy/). This draft assembly contained 4.5 MB of nucleotide sequence partitioned into 169 contiguous regions, from which 3671 putative proteins were derived. In December 2006, the gaps in the sequence were closed and the finished sequence is expected early in 2007.

As an indication of the unusual fermentation properties of *Clostridium phytofermentans* and its ability to decompose multiple components of plant biomass, we examined the genome sequence for evidence of carbohydrate uptake mechanisms. The genome of *Clostridium phytofermentans* contains over 100 ABC-type transport systems and 52 of these appear to be dedicated to transporting carbohydrates into cells. While some of these transport systems are specific for monosaccharides like glucose, fucose, or xylose, others are undoubtedly involved in the transport of disaccharides (e.g., cellobiose), trisaccharides, and tetrasaccharides. This exceptionally broad diversity of carbohydrate transport systems is unprecedented among microbes, and indicates that *Clostridium phytofermentans* is particularly well suited to decomposing cellulosic biomass.

Other Embodiments

It is to be understood that while the invention has been described in conjunction with the detailed description thereof, the foregoing description is intended to illustrate and not limit the scope of the invention, which is defined by the scope of the appended claims.

Other aspects, advantages, and modifications are within the scope of the following claims.

What is claimed is:

1. A method of making a fuel, the method comprising:
combining *Clostridium phytofermentans* cells and a lignocellulosic material in a medium; and
directly fermenting the lignocellulosic material under conditions and for a time sufficient to produce a fuel.

2. The method of claim 1, wherein the lignocellulosic material is selected from the group consisting of wood, wood pulp, papermaking sludge, paper pulp waste streams, particle board, grasses, rice hulls, bagasse, cotton, jute, hemp, flax, bamboo, sisal, abaca, straw, corn cobs, corn stover, distillers grains, leaves, wheat straw, coconut hair, algae, switchgrass, *Miscanthus*, legume plants, sorghum, biomass crops (Crambe), and mixtures thereof.

3. The method of claim 1, wherein the medium has dissolved therein constituents selected from the group consisting of growth factors, minerals, surfactants, chelating agents, and mixtures thereof.

4. The method of claim 1, wherein conditions include maintaining the medium at a temperature of less than about 45° C.

5. The method of claim 1, wherein conditions include maintaining a pH of the medium below about 9.5.

6. The method of claim 1, wherein the lignocellulosic material comprises a high molecular weight carbohydrate at a concentration in the medium of greater than 40 mM expressed as monosaccharide equivalents.

7. The method of claim 6, wherein the concentration of the high molecular weight carbohydrate is greater than 100 mM expressed as monosaccharide equivalents.

8. The method of claim 6, wherein the high molecular weight carbohydrate is selected from the group consisting of cellulose, microcrystalline cellulose, polygalacturonic acid, pectin, xylan, and mixtures thereof.

9. The method of claim 1, wherein the fuel comprises an alcohol selected from the group consisting of ethanol, n-propanol, isopropanol, n-butanol, and mixtures thereof.

10. The method of claim 1, wherein the lignocellulosic material is reduced in size prior to combining the material with the *Clostridium phytofermentans* cells.

11. The method of claim 1, further comprising combining a second type of microbe with the lignocellulosic material in the medium.

12. The method of claim 11, wherein the second microbe comprises a yeast or a bacterium different than *Clostridium phytofermentans*.

13. A method of making ethanol, the method comprising:
combining *Clostridium phytofermentans* cells and a lignocellulosic material in a medium; and
directly fermenting the lignocellulosic material under conditions and for a time sufficient to produce ethanol.

* * * * *